United States Patent [19]

Paap

[11] 4,301,400
[45] Nov. 17, 1981

[54] MICROWAVE WATER IN CRUDE MONITOR

[75] Inventor: Hans J. Paap, Houston, Tex.

[73] Assignee: Texaco Inc., White Plains, N.Y.

[21] Appl. No.: 106,585

[22] Filed: Dec. 26, 1979

[51] Int. Cl.³ .......................................... G01R 27/04
[52] U.S. Cl. ................................................ 324/58.5 A
[58] Field of Search ...................... 324/58.5 A, 58 A; 73/61.1 R

[56] References Cited

U.S. PATENT DOCUMENTS

| | | | |
|---|---|---|---|
| 3,498,112 | 3/1970 | Howard | 73/61.1 R |
| 3,644,826 | 2/1972 | Cornetet, Jr. | 324/58.5 A |
| 4,131,845 | 12/1978 | Pakulis | 324/58.5 A |

FOREIGN PATENT DOCUMENTS 253186 11/1970 U.S.S.R. .................... 324/58.5 A

*Primary Examiner*—Stanley T. Krawczewicz
*Attorney, Agent, or Firm*—Carl G. Ries; Robert A. Kulason; Ronald G. Gillespie

[57] ABSTRACT

A microwave water-in-crude monitor measures the percent quantity of water in crude oil flowing in a pipe line by causing the crude oil to flow through a measuring cell. A microwave transmitter is arranged with the measuring cell and transmits microwave energy through the measuring cell. A microwave receiver receives the energy transmitted through the measuring cell and provides a signal in accordance with the received energy. Apparatus connected to the microwave receiver provides a display of the water content of the crude oil in accordance with the signal from the microwave receiver.

5 Claims, 3 Drawing Figures

4,301,400

MICROWAVE WATER IN CRUDE MONITOR

BACKGROUND OF THE INVENTION

Field of the Invention

The present invention relates to monitors in general and, more particularly, to a water-in-crude monitor.

SUMMARY OF THE INVENTION

A microwave water-in-crude monitoring system measures the percent quantity of fresh water or salt water in crude oil flowing in a pipe line. The system includes a measuring cell arranged with the pipe line so that the crude oil flows through the measuring cell. A microwave transmitter subsystem is arranged with the measuring cell so that microwave energy is transmitted through the measuring cell. A microwave receiving subsystem provides a signal corresponding to received microwave energy. Apparatus connected to the microwave receiver provides an indication of the percentage of water in the crude oil.

The objects and advantages of the invention will appear more fully hereinafter from a consideration of the detailed description which follows, taken together with the accompanying drawings which follow, wherein one embodiment of the invention is illustrated by way of example. It is to be expressly understood, however, that the drawings are for illustration purposes only and are not to be construed as defining the limits of the invention.

DESCRIPTION OF THE INVENTION

A method of determining the fresh water or salt water content of flowing streams of gas free crude oil under the conditions encountered in well flow lines utilizes the measurement of microwave attenuation caused by water present in the crude stream. Dielectric relaxation of the water molecules at microwave frequencies causes severe attenuation of electromagnetic waves of centimeter wavelength. Attenuation of centimeter waves has been used to measure moisture content in many materials such as concrete and core slabs, see "Microwave Attenuation—A New Tool for Monitoring Saturations in Laboratory Flooding Experiments," by R. W. Parsons, Marathon Oil Company, Society of Petroleum Engineers Journal, Aug. 1975, pp. 302-310.

The propagation of a plane-parallel electromagnetic wave can be represented by the folllowing equations:

$$E = E_o e^{-\alpha x} \cdot e^{j2\pi(vt - \beta x/2\pi)}$$
$$H = H_o e^{-\alpha x} \cdot e^{j2\pi(vt - \beta x/2\pi)} \quad (1)$$

where E and H are the electric and magnetic field vectors, x and t the direction of propagation and propagation time in space and v the frequency of the wave. Obviously, the wave has a time period $T = 1/v$ and a space period $\lambda = 2\pi/\beta$ (wavelength). Also the wave is attenuated by the factor $e^{-\alpha x}$ as it proceeds along the x-direction. The attenuation factor $\alpha$ is a function of dielectric and magnetic characteristics of the propagating material at the frequency of the wave and is of interest only to the water-in-crude determination. Assuming no magnetic losses in the propagating materials which is certainly true for crude streams, the attenuation factor a is given by the following equation:

$$\alpha = (2\pi/\lambda_o)\{(k'/2)[(1 + (k''/k')^2)^{\frac{1}{2}} - 1]\}^{\frac{1}{2}},$$

where
$\lambda_o$ = wavelength in empty space (air),
$k'$ = relative dielectric constant, and
$k''$ = relative loss factor.

Figure 1:
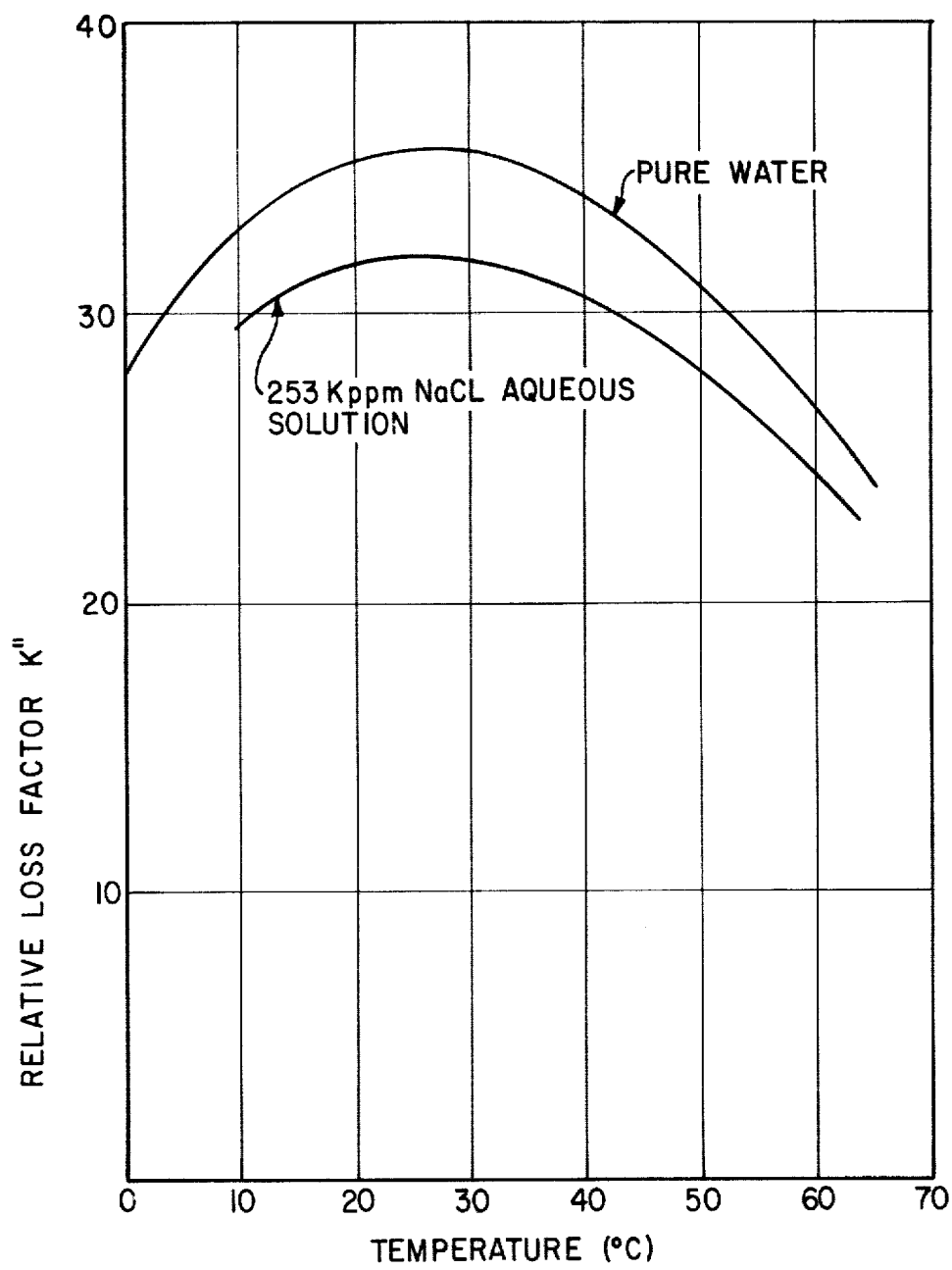
FIG. 1 is a plot of relative loss factor versus temperature at a particular wavelength.

The parameters $k'$ and $k''$ are dependent on the frequency of the wave, the temperature and the material composition of the propagating material. The hydrocarbons in crude oils have low values of $k'$ and $k''$ in comparison of those of water and aqueous solutions of sodium chloride. As an example $k''$, the relative loss factor, for pure water and for a 253 kppm aqueous NaCl solution is plotted versus temperature for a wavelength of 1.267 cm (23.68 GHz) in FIG. 1. Data for the plot was obtained from "The Dielectric Properties of Water in Solutions" by J. B. Hasted, S.M.M. El Sabeh, Transaction of the Faraday Society, V. 49, 1953, London. Note that the loss factor has a maximum at about 28° C. This maximum shifts to lower temperatures at lower frequencies and to higher temperatures at higher frequencies. Also it should be noted that the values for the almost saturated aqueous NaCl solution is only slightly lower than that for the pure water. Values of $k''$ for the hydrocarbons in most crude oils are less than about 0.05 at the above wavelength, as can be determined from "Tables of Dielectric Dispersion Data for Pure Liquids and Dilute Solutions" by Floyd Buckley et al, Nov. 1958, NTIS PB-188296.

The attenuation coefficient, $\alpha$, for the pure water and the 253 kppm NaCl solution were computed for the temperature range 0° to 60° C. (32° to 140° F.) at a wavelength of 1.267 cm. The attenuation coefficient for the liquid hydrocarbons in crude oils computes to less than 0.0013 cm$^{-1}$ over the same temperature range.

The following example calculation illustrates how microwave attenuation measurements may determine watercut at the wellhead or in the flow line to a GOSP unit. Based on PVT data for a well and assuming flow-line temperature and pressure near the wellhead of 150° F. and 500 psi, respectively, a liquid hydrocarbon volume of 30% of total flowing volume was computed. Any water produced was assumed to have a salinity of about 230 kppm NaCl. Microwave attenuation factors at a wavelength of 1.267 cm and above temperature were about 9 cm$^{-1}$ for the water, 0.0012 cm$^{-1}$ for the liquid hydrocarbons and negligible for the free gas in the flowline.

Consider now a microwave propagation path of 2 ft. (60.96 cm) through the flowing hydrocarbon water mixture in the flow line. Attenuation of the initial wave intensity $I_o$ to a value I along this pathlength due to various watercuts of the liquid hydrocarbons is tabulated in Table I hereinafter. The water content is expressed in pounds of salt in 1000 BBLS of crude (PTB). Table II shows data for 1 ft. path.

The data in Tables I and II are computed for the average composition of 30% liquid hydrocarbon volume and 70% free gas volume. However, flow conditions within the flow line vary in time (slug flow, dispersed flow, etc.). Therefore, the above data represent time averaged measurements and serve only to illustrate the strong effect of small watercuts within the crude. Refraction and reflection of the microwave on the dispersed phase are not taken into the computation but must be evaluated by experiments.

As can be seen in the data presented in Tables I and II, microwave attenuation measurements are capable of detection of watercuts of 100 PTB.

Figure 2:
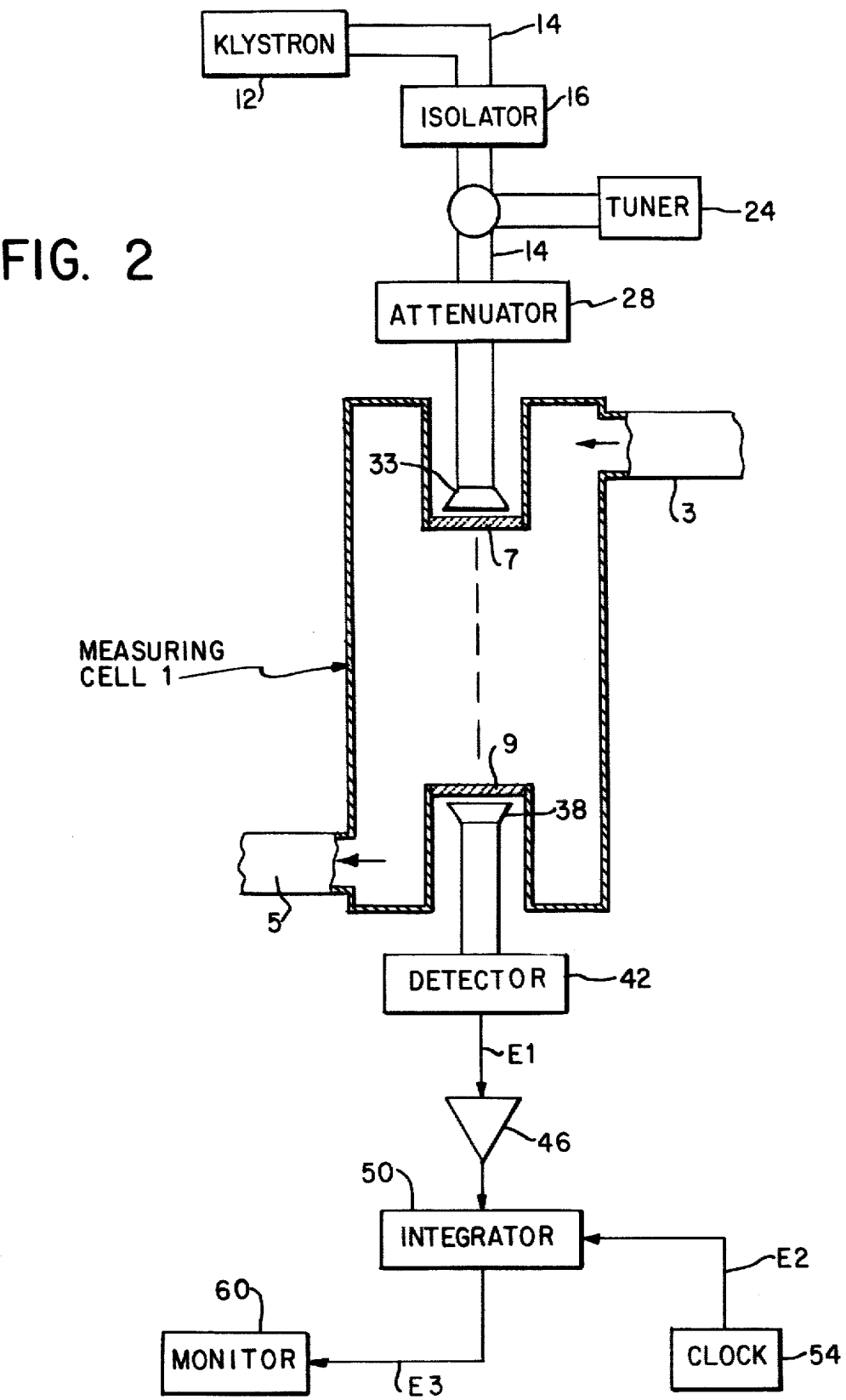
FIG. 2 is a simplified block diagram of a water in crude monitor constructed in accordance with the present invention.

A schematic of the basic microwave hardware for a simple attenuation measurement is shown in FIG. 2. Other embodiments are possible and will not be considered here. The measuring cell of FIG. 3 can be either permanently installed in a flowline or attached temporarily to the wellhead or flowline through proper valving. The microwave electronic and recording instrumentation could be separated from the cell and made portable.

TABLE I

| WATER CONTENT IN PTB'S | ATTENUATION $I/I_o$ |
|---|---|
| 10 | 0.981 |
| 100 | 0.828 |
| 200 | 0.686 |
| 500 | 0.390 |
| 1000 | 0.152 |
| 2000 | 0.023 |

A similar computation was made for a pathlength of only 1 ft.; these data are shown in Table II.

TABLE II

| WATER CONTENT IN PTB'S | ATTENUATION $I/I_o$ |
|---|---|
| 100 | 0.910 |
| 200 | 0.828 |
| 500 | 0.625 |
| 1000 | 0.390 |
| 2000 | 0.152 |
| 5000 | 0.009 |

Referring now to FIG. 2, oil flowing from a well head enters a measuring cell 1 by way of a pipe 3 and leaves cell 1 by way of a pipe 5. Cell 1 includes ceramic windows 7, 9. A conventional type klystron 12 provides microwave frequency radiation through wave guides 14 to an isolator 16. Isolator 16 stops reflected microwaves from entering klystron 12; a tuner 24 provides a mechanical type tuning for matching the transmission subsystem when isolator 16 provides microwaves to attenuator 28.

Attenuator 28 provides attenuated microwaves to a conventional horn antenna 33 which propagates the microwaves through window 7 and through window 9 to a second horn antenna 38. Horn antenna 38 provides the received microwaves to a microwave detector 42 which in turn provides an electrical signal E1 to an amplifier 46. The amplified signal from amplifier 46 is provided to an integrator 50 receiving pulses $E_2$ from a clock 54 and provides an integrated signal $E_3$ to a monitor 60.

Figure 3:
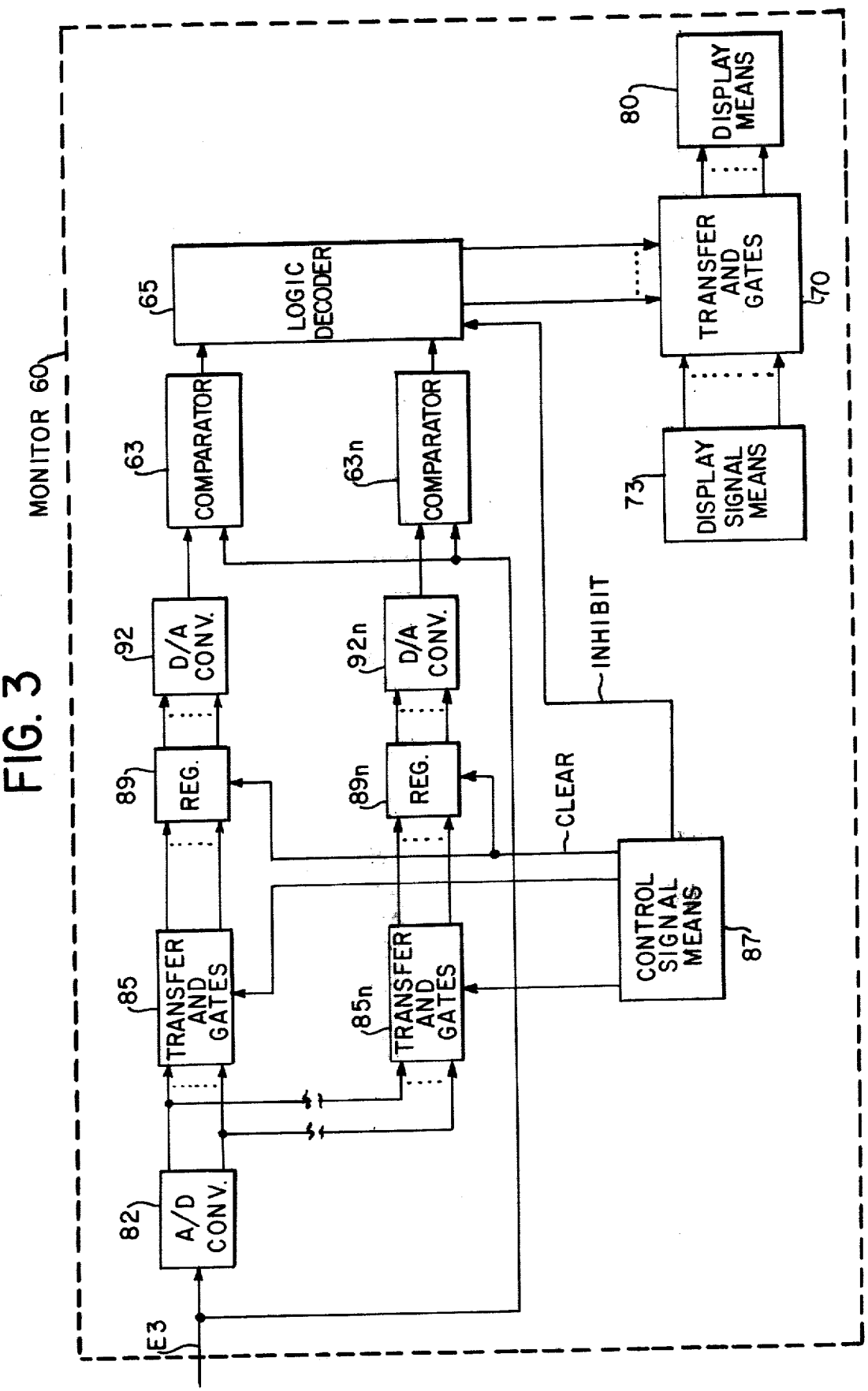
FIG. 3 is a detailed block diagram of the monitor shown in FIG. 2.

Referring now to FIG. 3, monitor 60 includes comparators 63 through 63n receiving signal $E_3$ and reference signals corresponding to different percentages of water or salt water in oil, as hereinafter explained. Comparators 63 through 63n represents a plurality of n comparators depending on the accuracy required. Comparators 63 through 63n provide output signals to a logic decoder 65 which decodes the output signals to provide control signals to transfer AND gates 70. Transfer AND gates 70 also receive groups of digital signals from display signal means 73. Each group of digital signals corresponds to a different percentage of water in the crude oil. When controlled by logic decoder 65, transfer AND gate 70 selects a particular group of digital signals and provides them to display means 80 to provide either a visual display or a printed display or both of the percentage of water in the crude oil. The details of display signal means 73 are not necessary to an understanding of the present invention. One version may include registers having prestored therein the desired digital contents.

The generation of the reference signals is as follows. Signal E3 is applied to an analog to digital converter 82 which provides digital signals, corresponding to signal E3, to transfer AND gates 83 through 85n. As noted before, the letter n represents the nth channel of a plurality of n channels. Transfer AND gates 85 through 85n are controlled by signals from a manually operative control signal means 87 to pass their received signals, at the appropriate time, from control signal means 87. Control signal means 87 also provides an inhibit signal to logic decoder 65 to prevent the generation of control signals by decoder 65 while the reference signals are being established. Registers 89 through 89n provide digital signals, corresponding to their contents, to digital-to-analog converters 92 through 92n, respectively. Converters 92 through 92n provide corresponding analog signals as the reference signals to comparators 63 through 63n, respectively.

In operation, pure crude oil or 100% water or mixtures of various percentages of oil and water are entered into measuring cell 1 during the calibration of the system. For example, when 100% crude oil is in measuring cell 1, the operator causes control signal means 87 to provide an enabling pulse to transfer AND gates 85 so that the digital signals from analog-to-digital converter 82 are provided to register 89 and enter register 89. Register 89 contents therefore correspond to 100% crude oil and comparator 63 receives a reference signal corresponding to 100% oil. At the other end of the scale, when pure water is in measuring cell 1, the operator provides an enabling signal from control signal means 87 to transfer AND gate 85n, causing them to enter register 89n so that the content of register 89n corresponds to 100% water. Similarly, the reference signal received by comparator 63n corresponds to 100% water.

At the start of each calibration period the operator causes control signal means 87 to provide a clear pulse to registers 89 through 89n and the inhibit signal to logic decoder 65. The inhibit pulse is terminated with the termination of the calibration operation.

The present invention as hereinbefore described is a water-in-crude monitoring system utilizing microwave techniques wherein a microwave signal is transmitted through the mixture of oil and water and the resultant detected signal is compared with known values for that signal.

What is claimed is:

1. A system for measuring the percent quantity of water in crude oil flowing in a pipe line comprising cell means arranged with pipe line so that the crude oil flows through the cell means, microwave transmission means spatially arranged with the cell means for transmitting microwave energy through the crude oil flowing through the cell means, receiver means spatially arranged with the cell means for receiving the transmitted energy and for providing a signal corresponding to the received energy, and means connected to the receiver means for providing an indication of the quantity of water in the crude oil, said indicating means includes means for providing reference signals, each reference signal corresponding to a different percent water content of the crude oil, comparing means connected to the receiver means and to the reference signal means for comparing the signal from the receiver means with the reference signals to provide a signal corresponding to the percent water content of the crude oil, decoding means connected to the comparing means for providing control signals in accordance with the signals from the comparing means, display signal means for providing display signals corresponding to different percent content of water of the crude oil, switching means connected to the decoding means and to the display signal means for selecting the proper display signals in accordance with the control signals from the decoding means to provide selected display signals, and display means connected to the switching means for providing a display in accordance with the selected display signals, and wherein said reference signals means include an analog-to-digital converter means connected to the receiver means for providing digital signals corresponding to the signal from the receiver means, a plurality of reference signal channels connected to the analog-to-digital converter means and controlled to store appropriate digital signals ccorresponding to known percent water volume of the crude oil, and control signal means connected to the plurality of reference signal channels and to the decoding means for controlling the plurality of reference signals channels for different known conditions of the crude oil and for inhibiting the decoding means while developing the reference signals.

2. A system as described in claim 1 in which the cell means includes a pair of ceramic windows arranged in the cell means so that the radiant energy is transmitted through one ceramic window and received by the receiver means through the other ceramic window.

3. A system as described in claim 2 in which the transmission means includes klystron means providing microwave output, wave guide means for conducting the microwaves from the klystron means, tuning means for tuning the microwaves, isolator means arranged between the tuning means and the klystron means for preventing feedback of microwaves to the klystron means, means receiving the microwaves for attenuating them, and first antenna means receiving the attenuated microwaves for transmitting the microwave energy through the one ceramic window.

4. A system as described in claim 3 in which the receiver means includes second antenna means arranged with the other ceramic window for receiving the transmitted energy, a detector coupled with the second antenna means provides a signal corresponding to the received microwave energy, an amplifier connected to the detector amplifies the signal from the detector, and integrating means connected to the amplifier, to the analog-to-digital converter means and to the comparing means for providing an integrated signal to the comparing means and to the analog-to-digital converter means in accordance with the signal from the amplifier, so as to cause the indicating means to provide the indication of the water content of the crude oil.

5. A system as described in claim 4 in which each reference signal channel includes transfer AND gates connected to the analog-to-digital converting means and to the control signal means for passing the digital signals from the analog-to-digital converter means in response to a signal from the control signal means, register means connected to the transfer AND gate and to the control signal means for being cleared by a clear signal from the control signal means and for entering the signals provided by the transfer AND gate means and for providing digital signals corresponding to its contents, and digital-to-analog converter means connected to the comparing means for converting the digital signals from the register to a corresponding reference signal.

* * * * *